(12) United States Patent
Ikeda

(10) Patent No.: US 8,588,491 B2
(45) Date of Patent: Nov. 19, 2013

(54) MEDICAL IMAGE PROCESSING APPARATUS

(75) Inventor: Yoshihiro Ikeda, Sakura (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 786 days.

(21) Appl. No.: 12/699,316

(22) Filed: Feb. 3, 2010

(65) Prior Publication Data

US 2010/0195880 A1 Aug. 5, 2010

(30) Foreign Application Priority Data

Feb. 4, 2009 (JP) ................................. 2009-024054

(51) Int. Cl.
*G06K 9/00* (2006.01)

(52) U.S. Cl.
USPC .......................................................... 382/131

(58) Field of Classification Search
None
See application file for complete search history.

(56) References Cited

U.S. PATENT DOCUMENTS

| | | | |
|---|---|---|---|
| 6,650,928 B1 * | 11/2003 | Gailly et al. ................... | 600/425 |
| 6,745,066 B1 * | 6/2004 | Lin et al. ........................ | 600/425 |
| 7,783,132 B2 * | 8/2010 | Nowinski et al. ............. | 382/294 |
| 8,019,142 B2 * | 9/2011 | Nowinski et al. ............. | 382/131 |
| 2005/0113680 A1 * | 5/2005 | Ikeda et al. .................... | 600/425 |
| 2005/0283070 A1 * | 12/2005 | Imielinska et al. ........... | 600/425 |
| 2007/0161886 A1 | 7/2007 | Kuth et al. | |
| 2007/0167731 A1 * | 7/2007 | Taxt et al. ..................... | 600/410 |
| 2008/0021502 A1 * | 1/2008 | Imielinska et al. ............... | 607/1 |
| 2008/0262344 A1 * | 10/2008 | Brummett ...................... | 600/426 |
| 2009/0129649 A1 * | 5/2009 | Djeridane ....................... | 382/131 |
| 2010/0158337 A1 * | 6/2010 | Burger et al. .................. | 382/131 |
| 2011/0015520 A1 * | 1/2011 | Meetz et al. ................... | 600/425 |
| 2011/0211742 A1 * | 9/2011 | Bredno et al. ................. | 382/128 |
| 2012/0078085 A1 * | 3/2012 | Xue et al. ....................... | 600/420 |

FOREIGN PATENT DOCUMENTS

| | | |
|---|---|---|
| JP | 62-201146 | 9/1987 |
| JP | 2005-131010 | 5/2005 |
| JP | 2005-131011 | 5/2005 |
| JP | 2005-296348 | 10/2005 |
| JP | 2005-328977 | 12/2005 |

(Continued)

OTHER PUBLICATIONS

Reichenbach, Jurgen R., "Acute Stroke Evaluated by Time-to-Peak Mapping during Initial and Early Follow-up Perfusion CT Studies", Nov./Dec. 1999.*

(Continued)

*Primary Examiner* — Robert Morgan
*Assistant Examiner* — Michael Tomaszewski
(74) *Attorney, Agent, or Firm* — Oblon, Spivak, McClelland, Maier & Neustadt, L.L.P.

(57) ABSTRACT

A storage unit stores four-dimensional image data indicative of an aged change in perfusion in a three-dimensional region including at least a part of a subject including a body axis thereof. A control unit analyzes a distribution of a TTP value of the perfusion concerning the coronal slice. The control unit calculates a difference value between the TTP values on both sides sandwiching the body axis on a straight line orthogonal to the body axis in the coronal slice. The control unit analyzes at least one of a distribution of the TTP value and a distribution of a characteristic value different from the TTP value in regard to a axial slice orthogonal to the coronal slice at a position of the straight line on which a maximum value in a plurality of difference values calculated is calculated.

11 Claims, 3 Drawing Sheets

(56) References Cited

FOREIGN PATENT DOCUMENTS

| JP | 2006-136506 | 6/2006 |
|---|---|---|
| JP | 2037-130462 | 5/2007 |
| WO | WO 2007/052634 A1 | 5/2007 |

OTHER PUBLICATIONS

Nasel, Christian, "A Standardized Method of Generating Time-to-Peak Perfusion Maps in Dynamic-Susceptibility Contrast-Enhanced MR Imaging", Oct. 1999.*

Konstas, Angelos A. MD, PhD, "CT Perfusion Imaging of Acute Stroke: The Need for Arrival Time Delay Insensitive and Standardized Postprocessing Algorithms?", Jan. 2010.*

Yanxi Liu, et al. "Automatic Extraction of the Central Symmetry (Mid-Sagittal) Plane from Neuroradiology Images"; CMU-RI-TR-96-40; The Robotics Institute Carnegie Mellon University; 1996; 31 pgs.

Jurgen R. Reichenbach, et al. "Acute Stroke Evaluated by Time-to-Peak Mapping during Initial and Early Follow-up Perfusion CT Studies"; American Journal of Neuroradiol, Nov./Dec. 1999; pp. 1842-1850.

Office Action issued May 14, 2013, in Japanese Patent Application No. 2009-024054 (with English Translation).

* cited by examiner

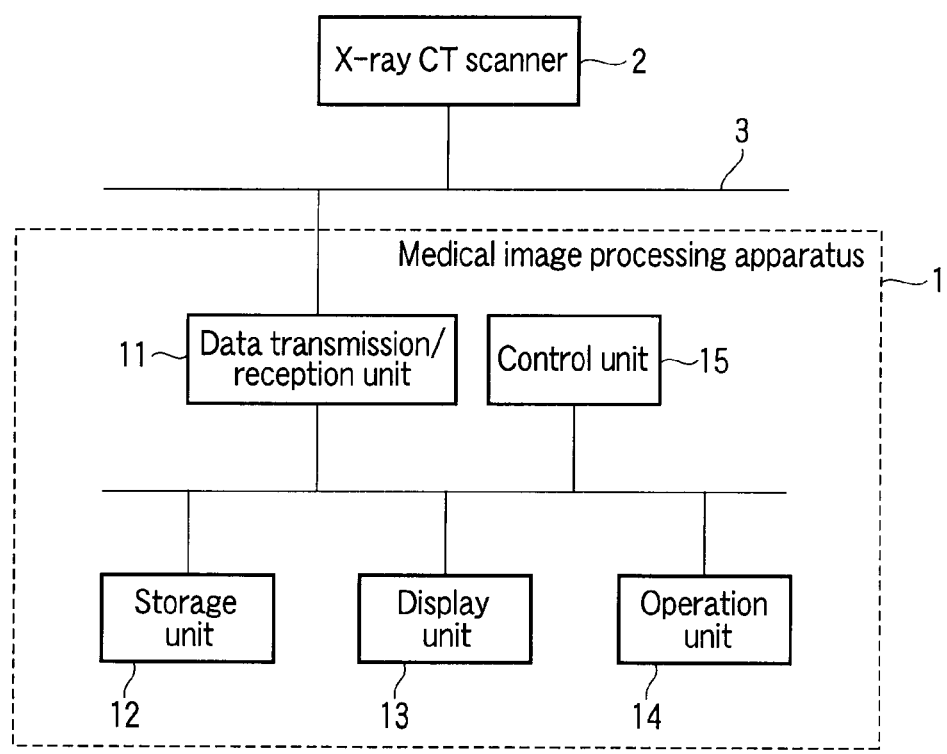
F I G. 1

MEDICAL IMAGE PROCESSING APPARATUS

CROSS-REFERENCE TO RELATED APPLICATIONS

This application is based upon and claims the benefit of priority from prior Japanese Patent Application No. 2009-024054, filed Feb. 4, 2009, the entire contents of which are incorporated herein by reference.

BACKGROUND OF THE INVENTION

1. Field of the Invention

The present invention relates to a medical image processing apparatus that is preferable for brain blood flow analysis (CT-perfusion or MR-perfusion) based on images obtained by an X-ray CT (computed tomography) scanner or an MRI (magnetic resonance imaging) device.

2. Description of the Related Art

In an X-ray CT scanner, realization of multiple X-ray detector rows has advanced, and a super multi-detector row system including 320 X-ray detector rows has appeared on the scene. In such a super multi-detector row system, for example, images of a subject region such as a brain can be substantially simultaneously acquired as many slices. Thus, for example, in CT-perfusion, time-series contrast medium concentration curves of an artery and a subject region are obtained based on four-dimensional image data that is acquired by repeatedly performing simultaneous imaging of many slices at a plurality of timings. Further, a blood flow volume, a blood volume and a blood average transit time distribution of the subject region are analyzed, and they are displayed as images. In the CT-perfusion utilizing the multi-detector row CT system, each of the many slices is subjected to the analysis, and results of the analysis are displayed after end of the analysis of all the slices. JP-A 2007-130462 (KOKAI) discloses a relevant technology.

Since four-dimensional image data obtained by a super multi-detector row system including, e.g., 320 rows has a massive data amount, the above-described perfusion analysis requires a very long time. Therefore, there is an inconvenience that the system is hard to be applied to a diagnosis of an acute symptom such as acute stroke.

BRIEF SUMMARY OF THE INVENTION

It is an object of the present invention to provide a medical image processing apparatus which makes the diagnosis using analyzed image concerning perfusion based on four-dimensional image data to start rapidly.

According to an aspect of the present invention, there is provided a medical image processing apparatus comprising: a storage unit which stores medical image data indicative of an aged change in perfusion in a three-dimensional region including at least a part of a subject including a body axis thereof; a first analysis unit which analyzes a distribution of a first characteristic value of the perfusion concerning a first slice along the body axis; a calculation unit which calculates a difference value between the first characteristic values on both sides sandwiching the body axis on a straight line orthogonal to the body axis in the first slice; and a second analysis unit which analyzes at least one of a distribution of the first characteristic value and a distribution of a second characteristic value different from the first characteristic value in regard to a second slice orthogonal to the first slice at a position of the straight line on which a maximum value in a plurality of difference values calculated by the calculation unit is calculated.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing a configuration of a medical image processing apparatus according to an embodiment of the present invention;

DETAILED DESCRIPTION OF THE INVENTION

Figure 2:
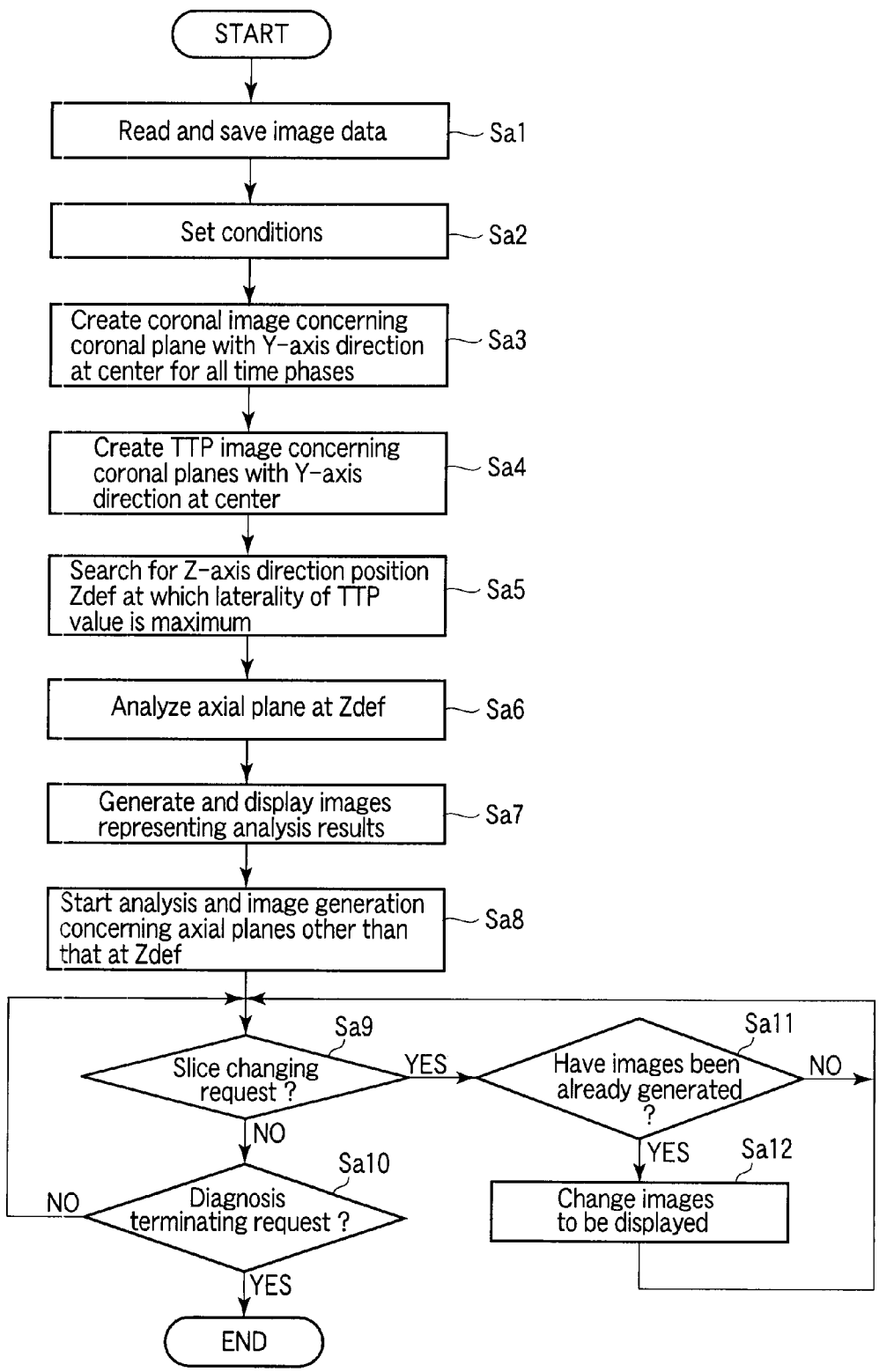
FIG. 2 is a flowchart of processing for brain blood flow analysis based on four-dimensional image data.

An embodiment according to the present invention will now be described with reference to the accompanying drawings.

FIG. 1 is a block diagram showing a configuration of a medical image processing apparatus 1 according to this embodiment.

This medical image processing apparatus 1 can communicate with an X-ray CT scanner 2 through a communication network 3. The X-ray CT scanner 2 includes multiple rows of X-ray detectors and has a function of substantially simultaneously imaging many slices in a three-dimensional region. Further, the X-ray CT scanner 2 has a function of repeatedly performing simultaneously imaging of many slices at a plurality of timings to generate four-dimensional image data. The medical image processing apparatus 1 carries put respective types of analysis processing for medical diagnoses based on image data generated by the X-ray CT scanner 2. The analysis processing performed by the medical image processing apparatus 1 includes at least processing for brain blood flow analysis based on the four-dimensional image data.

The medical image processing apparatus 1 includes a data transmission/reception unit 11, a storage unit 12, a display unit 13, an operation unit 14 and a control unit 15.

The data transmission/reception unit 11 includes a communication device that transmits/receives data through the communication network 3. As this communication device, an existing LAN board conforming to a universal standard can be used. The data transmission/reception unit 11 communicates with the X-ray CT scanner 2 through the communication network 3. Furthermore, the data transmission/reception unit 11 reads image data generated by the X-ray CT scanner 2 from the X-ray CT scanner 2 under control of the control unit 15.

The storage unit 12 includes a storage device such as a semiconductor memory or a hard disk. The storage unit 12 stores image data read from the X-ray CT scanner 2 or data representing an analysis result image generated as a result of analysis processing.

The display unit 13 includes a display device such as a liquid crystal display unit. The display unit 13 displays an image represented by data stored in the storage unit 12 or various kinds of information which should be presented to a user under control of the control unit 15.

The operation unit 14 includes an input device such as a keyboard or a mouse. The operation unit 14 inputs various kinds of instructions or information which are utilized to operate various functions of the medical image processing apparatus 1 by a user in response to an operation of the user.

The control unit 15 controls each unit in the medical image processing apparatus 1 to realize various functions such as reading of image data from the X-ray CT scanner 2 or analysis processing based on this read image data. The control unit 15 includes the following functions for brain blood flow analysis based on four-dimensional image data. One of the functions is to analyze a distribution concerning a first slice along a body axis of a subject having a first characteristic value of perfusion. One of the functions is to calculate a difference value between the first characteristic values on both sides sandwiching the body axis on a straight line orthogonal to the body axis in the first slice. One of the functions is to analyze at least one of a distribution of the first characteristic value and a distribution of one or more types of second characteristic values different from the first characteristic value in regard to a second slice orthogonal to the first slice at a position of the straight line on which a maximum value in the plurality of difference values is calculated.

It is to be noted that, in this embodiment, the perfusion is a blood flow to which a contrast medium has been administered, the first slice is a coronal slice, the second slice is an axial slice, the first characteristic value is a TTP (time to peak) value concerning a concentration of the contrast medium, the second characteristic values are a blood flow volume, a blood volume and an average transit time.

It is to be noted that the medical image processing apparatus 1 can be realized by utilizing a general-purpose computer device as basic hardware. Further, various functions of the control unit 15 can be realized by allowing a processor mounted on the computer device to execute a program written for realizing various functions. At this time, in the medical image processing apparatus 1, the program may be installed in the computer device in advance to be realized, or the program may be recorded in a removable recording medium such as a magnetic disk, a magneto optical disk, an optical disk or a semiconductor memory, or the program may be distributed through a network, or the program may be appropriately installed in the computer device to be realized. It is to be noted that part or all of the respective functions may be realized by hardware such as a logic circuit. Moreover, each of the respective units may be realized by combining hardware and software control.

An operation of the thus configured medical image processing apparatus 1 will now be described.

FIG. 2 is a flowchart showing a processing procedure of the control unit 15 in processing for brain blood flow analysis based on four-dimensional image data.

At a step Sa1, the control unit 15 operates the data transmission/reception unit 11 to read four-dimensional image data generated by the X-ray CT scanner 2 from the X-ray CT scanner 2 and stores this four-dimensional image data in the storage unit 12. In this embodiment, a three-dimensional region as an imaging target of the four-dimensional image data is a brain.

At a step Sa2, the control unit 15 sets various conditions for the brain blood flow analysis. As the conditions set here, there is, e.g., an arterial/venous ROI (region of interest).

At a step Sa3, the control unit 15 creates coronal images concerning the three-dimensional region, i.e., a coronal plane with a Y-axis direction of the brain at the center for all time phases of the four-dimensional image data. These coronal images represent a distribution of CT values in the coronal plane, i.e., a distribution of a contrast medium concentration. The coronal image created here serves as a coronal slice image of a region including a temporal lobe of the brain. It is to be noted that a coronal slice of a frontal lobe or a coronal slice of an occipital lobe may be used. In short, at the step Sa3, the control unit 15 creates coronal images concerning a coronal plane at any position in the Y-axis direction of the brain.

At a step Sa4, the control unit 15 creates TTP images concerning the same coronal plane based on the plurality of coronal images generated at the step Sa3. The TTP image is an image representing a distribution of each TTP value indicative of an appearance time required for the contrast medium concentration to reach a peak value from a reference time point in the coronal plane. The TTP value can be acquired by obtaining a concentration curve indicative of an aged change in the contrast medium concentration concerning the same position in the coronal plane and measuring an appearance time from a reference time point to a time point that a peak appears in this concentration curve. It is to be noted that the reference time point may be arbitrary as long as a common reference time point is applied when obtaining TTP values at respective positions in the coronal plane. In the thus created TTP image, the laterality occurs in an unusual region in any case.

Figure 3:
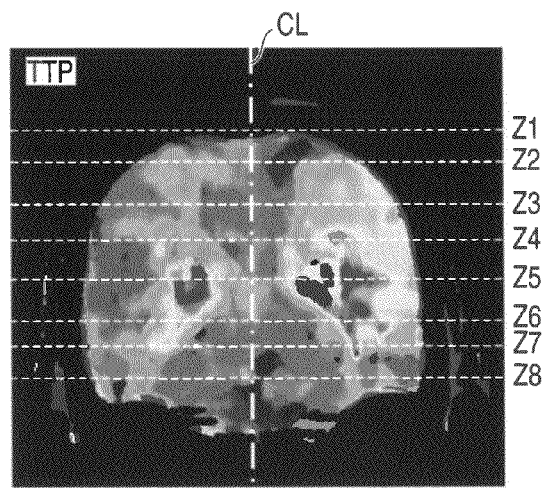
FIG. 3 is a view showing an example of a TTP image.

Thus, at a step Sa5, the control unit 15 retrieves a position Zdef in a Z-axis direction (a body-axis direction) where the laterality of the TTP value becomes maximum. Specifically, the control unit 15 first determines such a plurality of Z-axis direction positions Z1, Z2 . . . , Zn as shown in FIG. 3. These Z-axis direction positions Z1 to Zn can be arbitrarily determined, but the control unit 15 typically focuses on Z-axis direction positions of a plurality of axial slices or Z-axis direction positions of some of a plurality of axial slices. Additionally, the control unit 15 calculates a difference value of left and right TTP values sandwiching a central line (a line parallel to the body axis or a central line dividing the brain into left and right hemispheres) CL of the TTP image in regard to each of these Z-axis direction positions Z1 to Zn. This difference value can be obtained as a difference value of average values of TTP values in left and right regions, for example. Further, the control unit 15 selects a maximum value from the difference values concerning the respective Z-axis direction positions Z1 to Zn, and the Z-axis direction position for which the difference value selected as the maximum value is obtained is determined as Zdef.

At a step Sa6, the control unit 15 analyzes a blood flow volume, a blood volume and an average transit time in regard to an axial plane at the Z-axis direction position Zdef. It is to be noted that analysis targets may be just one or two selected from the blood flow volume, the blood volume and the average transit time, or other characteristic values concerning the blood flow may be analyzed.

Figure 4:
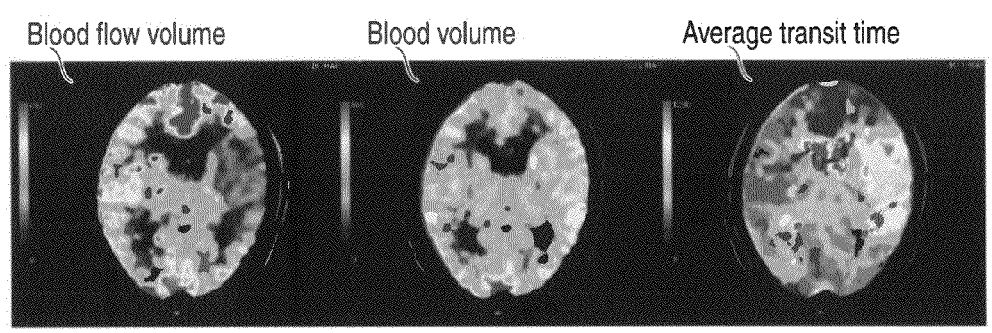
FIG. 4 is a view showing a display example of axial images representing results of perfusion analysis.

At a step Sa7, the control unit 15 generates images representing results of the above-described analysis and displays them in the display unit 13. Here, axial images representing distributions of the analyzed blood flow volume, blood volume and average transit time in the axial plane are generated, and these three axial images are displayed in the display unit 13. FIG. 4 is a view showing a display example in the display unit 13. FIG. 4 shows an example of aligning and simultaneously displaying the three axial images. However, a display conformation of the axial images in this example may be arbitrary. For example, one of the three axial images alone may be displayed in the display unit 13, and the axial image displayed in the display unit 13 may be changed in response to a change instruction from a user.

In a state where the axial images representing the analysis results concerning the Z-axis direction position Zdef are displayed in the display unit 13, the control unit 15 starts perfusion analysis of axial planes at Z-axis direction positions other than the Z-axis direction position Zdef and generation of axial images representing results of the analysis. Then, remaining axial planes can be arbitrarily determined as targets for the perfusion analysis and the axial image generation in an arbitrary order. However, adopting one of the following two conditions is clinically preferable.

(1) Axial planes at positions close to the Z-axis direction position Zdef are prioritized.

(2) Some axial planes which are not adjacent to each other are prioritized, and other axial planes are processed later.

In case of (1), since a region near the Z-axis direction position Zdef is processed by priority, this condition is beneficial when heavily making allowance for a tendency of a blood flow in this region and performing a diagnosis. On the other hand, in case of (2), since a wider region than that in (1) is processed, this condition is beneficial when making allowance for a tendency of a blood flow in the wider region and performing a diagnosis. Thus, although (1) or (2) may be fixedly applied, selectively applying (1) or (2) in response to a request from a user enables a flexible operation according to the user's needs, which is convenient.

The control unit 15 performs display of axial images in the display unit 13 and generation of new axial images in parallel, and it further waits until changing the slice of the axial images to be displayed is requested or terminating the diagnosis is requested at a step Sa9 and a step Sa10.

When the user operates the operation unit 14 to request changing the slice, the control unit 15 advances from the step Sa9 to a step Sa11. At the step Sa11, the control unit 15 confirms whether axial images to be newly displayed have been already generated. Further, if the corresponding axial images have been already generated, the control unit 15 changes the displayed images in the display unit 13 in order to display the corresponding axial images at a step Sa12. Then, the control unit 15 returns to the standby mode in the step Sa9 and the step Sa10. However, if the axial images to be newly displayed have not been generated yet, the control unit 15 returns to the standby mode in the step Sa9 and the step Sa10 without effecting the processing in the step Sa12. Of course, an operation for notifying the user that the requested images have not been generated yet may be carried out in this case.

Furthermore, when the user operates the operation unit 14 to request the termination of the diagnosis, the standby mode in the step Sa9 and the step Sa10 is finished at the step Sa10, thereby terminating the processing depicted in FIG. 2.

Thus, according to this embodiment, when the analysis of one slice and the generation of axial images representing results of the analysis are terminated, the axial images generated at this step are displayed prior to termination of the same processing of another slice. Therefore, the user can very rapidly confirm results of the perfusion analysis without waiting for completion of the processing of all slices. Moreover, according to this embodiment, since an axial slice which may highly possibly have a lesion is detected from coronal images of one slice by utilizing a property that a value of an analysis result differs depending on a left or right hemisphere in a slice having a lesion, a beneficial medical diagnosis can be possibly made based on axial images which are displayed first. As a result, using the medical image processing apparatus 1 according to this embodiment enables adequately making a diagnosis of an acute case such as acute stroke.

According to this embodiment, when a user is making a medical diagnosis based on axial images of a preceding slice, analysis and image generation of remaining axial slices are performed in the background. Therefore, even if an appropriate medical diagnosis cannot be made from the thus selected axial slice alone, allowances can be made for results of the perfusion analysis of other axial slices to carry out a medical diagnosis.

This embodiment can be modified in many ways as follows.

The four-dimensional image data used for the brain blood flow analysis may be generated by a modality which is different from the X-ray CT scanner 2 such as an MRI device.

The function for the brain blood flow analysis based on the four-dimensional image data may be implemented as a function of a modality, e.g., the X-ray CT scanner 2.

In place of the TTP image, it is possible to use an image representing a distribution of one of a maximum value of a contrast medium concentration, an appearance time from a reference time point to a time point that the contrast medium concentration starts increasing, a blood flow volume, and an average transit time within a coronal plane.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical image processing apparatus comprising:
a storage unit which stores medical image data indicative of an aged change in perfusion in a three-dimensional region including at least a part of a subject including a body axis thereof;
a first generation unit configured to generate a first slice along the body axis;
a first analysis unit which analyzes a distribution of a first characteristic value of the perfusion in the first slice along the body axis;
a calculation unit which calculates a difference value between the first characteristic values on both sides sandwiching the body axis on a straight line orthogonal to the body axis in the first slice;
a second generation unit configured to generate a second slice orthogonal to the first slice at a position on the straight line which is a maximum value in a plurality of difference values calculated by the calculation unit;
a second analysis unit which analyzes at least one of a distribution of the first characteristic value and a distribution of a second characteristic value different from the first characteristic value, with regard to the second slice orthogonal to the first slice, at the position on the straight line;
a third generation unit configured to generate an image corresponding to the second slice; and
a display unit configured to display the image and information corresponding to at least one of the distribution of the first characteristic value and the distribution of a second characteristic value.

2. The apparatus according to claim 1, wherein the second analysis unit analyzes at least one of the distribution of the first characteristic value and the distribution of the one or more types of the second characteristic values different from the first characteristic value in regard to one or more third slices which are parallel to the second slice and different from the second slice after the end of the analysis of the distribution concerning the second slice.

3. The apparatus according to claim 1, wherein the third generation unit is further configured to generate an image representing the distribution of the characteristic value analyzed by the second analysis unit.

4. The apparatus according to claim 2, wherein the third generation unit is further configured to generate an image representing the distribution of the characteristic value analyzed by the second analysis unit.

5. The apparatus according to claim 1, wherein the first characteristic value is an elapsed time from a reference time point to a time point that a pixel value in the medical image data reaches peak value.

6. The apparatus according to claim 1, wherein the first characteristic value is an elapsed time from a reference time point to a time point that a pixel value in the medical image data increases to a specified value smaller than a peak value.

7. The apparatus according to claim 1, wherein the first characteristic value is a peak value of a pixel value in the medical image data.

8. The apparatus according to claim 1, wherein the second characteristic value is a volume of the perfusion.

9. The apparatus according to claim 1, wherein the second characteristic value is an average transit time of the perfusion.

10. A medical image processing apparatus comprising:
- a storage unit which stores medical image data indicative of an aged change in a contrast medium concentration in blood in a three-dimensional region including at least a part of a subject including a body axis thereof;
- a coronal image generation unit which generates a coronal image representing a distribution of an elapsed time from a reference time point to a time point that the contrast medium concentration reaches a peak value in regard to one coronal slice;
- a calculation unit which calculates a difference value between the elapsed times on both sides sandwiching the body axis on a straight line orthogonal to the body axis within the coronal image;
- an axial slice generation unit configured to generate an axial slice at a position on the straight line which is a maximum value in a plurality of difference values calculated by the calculation unit;
- an axial image generation unit which generates an axial image representing a distribution of one of a flow volume of the blood, a volume of the blood and an average transit time of the blood with regard to the axial slice corresponding to the position on the straight line; and
- a display unit configured to display the axial image representing the distribution of one of the flow volume of the blood, the volume of the blood and the average transit time of the blood.

11. A medical image processing apparatus comprising:
- a storage unit which stores medical image data indicative of an aged change in a contrast medium concentration in blood in a three-dimensional region including at least a part of a subject including a body axis thereof;
- a coronal image generation unit which generates a coronal image representing a distribution of an elapsed time from a reference time point to a time point that the contrast medium concentration reaches a peak value in regard to one coronal slice;
- a calculation unit which calculates a difference value between the elapsed times on both sides sandwiching the body axis on a straight line orthogonal to the body axis within the coronal image;
- an axial slice generation unit configured to generate an axial slice at a position on the straight line which is a maximum value in a plurality of difference values calculated by the calculation unit;
- an axial image generation unit which generates at least two axial images representing distributions of at least two of a flow volume of the blood, a volume of the blood and an average transit time of the blood, respectively, in regard to the axial slice corresponding to the position on the straight line; and
- a display unit configured to display the axial image representing the distribution of one of the flow volume of the blood, the volume of the blood and the average transit time of the blood.

* * * * *